United States Patent [19]

Coody

[11] Plant 5,188

[45] Feb. 7, 1984

[54] PLANT OF THE ARACEAE FAMILY

[76] Inventor: Robert J. Coody, Rte. 1, Box 136, Fort Lawn, S.C. 29714

[21] Appl. No.: 380,062

[22] Filed: May 20, 1982

[51] Int. Cl.[3] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new plant of the *Spathiphyllum* species is somewhat smaller in size than that of the 'Mauna Loa' variety and has foliage with variegated leaf blades that have a basic chlorophyllous field containing streaks and blotches which in colors are lighter than those of the basic chlorophyllous field, and an inflorescence with a spathe that shortly after initial expansion is provided with variegated blades which have a basic achlorophyllous field that contains chlorophyllous streaks and blotches and merges distally in the spathe with a chlorophyllous tip area, spathe coloration changing as the spathe matures to provide variegated blades that have a basic chlorophyllous field which contains chlorophlyllous and nearly achlorophyllous streaks and blotches that are generally lighter in colors than those found in the basic chlorophyllous field of a mature spathe.

7 Drawing Figures

The invention relates to a new and distinct plant variety of the Araceae family and which has been named the *Araceae Spathiphyllum* 'Carolynia' by the inventor.

Certain plant varieties of the Araceae family are well known in the foliage plant market and among these is the 'Mauna Loa' variety of the *Spathiphyllum* species of the family. This variety is sometimes called the 'White anthurium' and is characterized among other things by foliage with leaf blades that have a solid green field and an inflorescence with a spathe which upon initial expansion has a basic white field in the blade area that sometimes merges distally in the spathe with a small amount of green coloration at the tip of the spathe.

The variety forming the subject matter of this application was developed from a sport or bud variation that appeared on a specimen of the 'Mauna Loa' variety and a general objective of the invention has been to provide a variety of the *Spathiphyllum* species which would be distinguishable from the other known varieties of this species and suitable for sale in the foliage plant marketplace.

Through successive propagations, it has been ascertained that specimens of the new plant variety generally resemble the specimens of the parent variety but are distinguishable from the parent variety and other related varieties known to the inventor by a growth habit which combines the following principal characteristics:

1. A plant specimen which in size is generally smaller than those of the 'Mauna Loa' variety of the *Spathiphyllum* species, 2. Foliage that includes leaf blades which are variegated and provided with a basic chlorophyllous field that contains streaks and blotches which in colors are generally lighter than those of the basic chlorophyllous field and which also vary in color, pattern and size within the leaf blades and from one leaf blade to the next, and 3. An inflorescence with a spathe that shortly after initial expansion is provided with variegated blades which have a basic achlorophyllous field that contains chlorophyllous streaks and blotches and merges distally in the spathe with a chlorophyllous tip area which extends proximally in the leaf blade further than that of the 'Mauna Loa' variety of the *Spathiphyllum* species, the spathe coloration changing as the spathe matures to provide variegated blades that have a basic chlorophyllous field which contains chlorophyllous and nearly achlorophyllous streaks and blotches that are generally lighter in colors than those found in the basic chlorophyllous field.

The accompanying drawings serve by color photographic means to illustrate the new plant variety and wherein one sheet illustrates a fourteen (14) month old specimen of the new plant variety and which has a mature spathe. The remaining six sheets illustrate the color in a spathe and spadix of the new plant variety on the fourth day after initial expansion of the spathe, on the 18th day after initial expansion and finally on the 35th day after expansion.

The following is a detailed description of the new plant variety with colors and hues, unless otherwise clearly indicated by the text through the absence of color notations, being named in accord with the ISCC-NBS Method of Designating Colors, (U.S. Department of Commerce, National Bureau of Standards, Circular 553, Nov. 1, 1955) the named colors being interpreted from Munsell Color Notations determined from numeric color designations derived by comparison with the color specimens in the Munsell Limit Color Cascade that is currently published by the Munsell Color Company, Inc., of Baltimore, Md. The description is further based on the observation of plant specimens which range from four to eight months in age from initial propagation of offshoots that were grown to mature specimens in Fort Lawn, SC.

DETAILED PLANT DESCRIPTION

Name: *Araceae Spathiphyllum* (cv) 'Carolynia'.

Origin: Sport or bud variation that appeared on a plant specimen of the variety known as *Spathiphyllum* 'Mauna Loa'.

Classification:

A. *Botanic.*—*Spathiphyllum* (Euspathiphyllum) *hybrida incertae sedis* Arum family (Araceae).

B. *Commercial.*—Foliage plant.

Plant form: Herbaceous, tropical, perennial evergreen with frequent adventitious roots, an ascending compact primary axis with frequent tillering at the base and erectopatent leaves that are surmounted by a spathoid inflorescence.

Plant size:

A. *Leaf spread.*—40–60 cm. in overall diameter at time of first flowering after propagation.

B. *Mature foliage height.*—20–35 cm. at time of first flowering after propagation.

C. *Inflorescence length.*—40–60 cm. at time of first flowering after propagation.

Roots: Adventitious roots that are freely formed from cuttings and with the mature plants usually having a non-aerial fibrous root system.

Stems: Rhizomatous with ascending tendencies.

Leaves:

A. *General.*—Simple, with a basal petiole sheath and a swollen geniculum that is located below and proximate to the lamina or blade.

B. *Arrangement.*—Alternate, and commonly with 2/5 phyllotaxy.

C. *Margins.*—Entire with undulate tendencies.

D. *Venation.*—1. General: Pinnate with a prominent midrib, secondary veins that are embedded at the adaxial side and prominent at the abaxial side of the leaf blade, and tertiary veins that are parallel to the secondary veins and usually embedded at both the adaxial and abaxial sides of the leaf blade, the secondary and tertiary veins being joined by cross veins that provide a scalariform arrangement with some irregularly reticulated tendencies. 2. Shape and Arrangement: (a) Midrib — Tapering distally and being canaliculate at the adaxial side and prominently keeled at the abaxial side of the leaf blade throughout most of its length dimension, the abaxial arch usually being semicircular and the adaxial groove usually being narrowly semi-elliptic to elliptic so that the arrangement provides a distally extending concavo-convex cross section at the proximal end of the midrib. (b) Lateral veins — Usually 9–13 secondary veins from each side of the midrib and located at intervals along the midrib which are usually 7–14 mm., the tertiary veins being usually spaced apart at 1–3 mm. intervals. 3. Midrib colors: (a) General — Usually concolorous or nearly concolorous on the adaxial side with the basic chlorophyllous field found in the leaf blades, and usually concolorous along the abaxial keel of the midrib with the abaxial surface of the geniculum. (b) Adaxial side — Commonly moderate olive green (21-14, 22-13, 22-14), dark olive green (20-15), dark yellow green (20-14, 18-14, 19-14), very dark yellowish green (18-15, 19-15), deep yellow green (21-12), strong yellow green (22-10, 22-11, 22-12), vivid yellow green (22-10), and/or deep yellowish green (20-12, 18-13, 19-13, 20-11). (c) Abaxial side — Commonly vivid yellow green (21-6, 22-5, 22-6, 23-5, 23-6, 23-9), brilliant yellowish green (20-3), brilliant yellow green (20-4, 20-5, 21-4, 21-5, 21-3, 23-3, 23-4, 22-3, 22-4), and/or strong yellow green (23-10, 23-11).

E. *Shape.*—1. General: Elliptic to lanceolate with occasional ovate tendencies. 2. Leaf apices: Attenuated acuminate with a weakly canaliculate to subtubulose tip. 3. Leaf bases: Symmetric and obtuse with oblique tendencies, and usually being decurrent well into the geniculum.

F. *Petioles.*—1. General: Provided with a fleshy basal sheath that extends for approximately two-thirds of the petiole length, and with a geniculum that merges into the midvein. 2. Shape: Generally elongated with the sheath surrounding the next emerging leaf during vernation and thereafter becoming free above the node as the leaf spreads and the sheath rolls in upon itself, the sheath becoming supervolute at its proximal end and being decurrent and somewhat conduplicate distally thereof to the terete, nonsheathing portion of the petiole, the nonsheathing portion abruptly increasing in diameter distally of the sheath to form an elongated terete geniculum which merges imperceptibly with the midvein at the abaxial side of the leaf and to which the blade is attached at the adaxial side of the leaf by two elongated adaxial decurrent blade extensions. 3. Texture: Glabrous and smooth. 4. Size (4–7 month old specimens): (a) Diameter — Usually about 3–4 mm. intermediate the sheath end of the geniculum. (b) Length (insertion to leaf blade) — Usually 10–19 cm. with the sheath length being about 6–14 cm. and the geniculum length being about 2–4 cm. 5. Color: (a) General — Usually concolorous or nearly concolorous with a basic chlorophyllous field on the adaxial side of the blade in the area proximate the geniculum and with a visibly lighter color for the geniculum. (b) Area proximate to geniculum — Commonly deep yellowish green (18-13, 19-13, 20-13), dark yellowish green (18-14, 19-14, 20-14), very dark yellowish green (18-15, 19-15), moderate olive green (21-14, 22-13), and/or dark olive green (20-15). (c) Geniculum — Commonly vivid yellowish green (18-6, 18-7, 18-8, 19-5, 19-6, 19-7, 19-8, 20-7, 20-8, 20-9), brilliant yellowish green (19-5, 20-3, 20-4), brilliant yellow green (20-4, 20-5, 21-4, 21-5, 22-3, 22-4), vivid yellow green (20-6, 21-6, 21-7, 21-8, 21-9, 21-10, 22-10, 23-7, 23-8, 23-9, 23-10), strong yellow green (21-11, 22-10, 22-11, 22-12), and/or deep yellow green (21-12, 22-12).

G. *Leaf blade.*—1. General: Variegated and chartaceous laterally of midrib and between the secondary veins. 2. Texture and shape: (a) Upper epidermis — Glabrous with scattered, nearly microscopic hyaline waxy excrescences and somewhat sulcate along the secondary veins. (b) Lower epidermis — Glabrous and weakly glaucous, the surface being ridged along the midvein and secondary veins and generally planar in the tertiary vein areas. 3. Size (4–7 month specimens): (a) Length — Usually about 15–25 cm. between proximal and distal ends. (b) Width — Usually about 6–8 cm. across the broadest expanse. 4. Color: (a) General — Variegated with basic chlorophyllous field containing streaks and blotches that vary from achlorophyllous to chlorophyllous and with colors that are somewhat lighter than those of the basic chlorophyllous field, the blotches and streaks usually following the secondary veins, and varying in color, pattern and size within any leaf and from one leaf to the next, the colors and patterns being somewhat obscured at the abaxial side of the blade by the translucent and glaucous nature of the lower epidermis. (b) Basic chlorophyllous field — Commonly deep yellowish green (18-13, 19-13, 20-13), dark yellowish green (18-14, 19-14, 20-14), very dark yellowish green (18-15, 19-15), dark olive green (20-15), deep yellow green (21-12, 21-13, 22-12), moderate olive green (21-14, 22-13), strong yellow green (22-10, 22-11, 22-12), and/or vivid yellow green (22-10). (c) Streaks and splotches — Commonly vivid yellowish green (19-6, 19-7, 19-8, 19-9, 20-7, 20-8, 20-9), light yellow green (20-2, 21-2, 23-2), very light yellowish green (20-2), brilliant yellowish green (20-3, 20-4), brilliant yellow green (20-4, 20-5, 21-3, 21-4, 21-5, 22-3, 22-4, 23-3, 23-4), vivid yellow green (20-6, 21-6, 21-7, 21-8, 21-9, 21-10, 22-5, 22-6, 22-7, 22-8, 22-9, 22-10, 23-5), strong yellow green (21-11, 22-10, 22-11, 22-12), and/or deep yellow green (21-12, 21-13, 22-12).

Inflorescence form: Axillary, peduncle bearing spathe with a stiped spadix the lower portion of the peduncle being enclosed within the petiolar sheath of the leaf and the peduncle emerging below the distal end of the sheath.

Peduncle:

A. *General.*—Erect, rigid and succulent.

B. *Texture.*—Smooth to faintly striate (under 10x magnification) and glabrous.

C. *Shape.*—Terete and weakly tapered upwardly.

D. *Size.*—1. Length: Usually 35–45 cm. 2. Diameter: Usually 2.5–4 mm. in the area proximate to the spathe and 3.5–5 mm. at the emergence from the petiolar sheath of the subtending leaf.

E. *Color.*—Commonly strong yellow green (21-11, 22-12, 22-10), deep yellow green (22-12), moderate yellow green (Centroid Chip No. 120), and/or vivid yellow green (22-10).

Pedicels: None.

Spathe:

A. *Pinnately veined with prominent midvein.*—Chartaceous between secondary veins, and tightly in-rolled upon the spadix prior to expansion, the expanded spathe being concave and subtending the spadix supporting stipe.

B. *Texture.*—Smooth with secondary veins that are embedded at the adaxial side and prominent at the abaxial side, and with poculous indentations and rises attributable to the tight roll upon the spadix being visible on the adaxial and abaxial sides after expansion.

C. *Shape.*—1. General: Ovate to elliptic with a facial depression upon expansion and a tendency to be asymmetric. 2. Apices: Attentuated acuminate and frequently with a partial to a full twist, the tip being canaliculate and commonly terminating in a small evanescent vestige that is usually dead. 3. Bases: Asymmetric, decurrent and oblique.

D. *Size.*—1. Length: Usually 10–15 cm. long. 2. Width: Usually 5–7 cm. across the widest portion when flattened. 3. Depression depth: Usually 2–3 cm. (maximum).

E. *Color.*— 1. General: Variegated with a basic achlorophyllous field containing random splotches and streaks shortly after initial expansion, the basic field merging distally in the spathe with a chlorophyllous tip area that extends proximally in the leaf blade further than commonly found in the 'Mauna Loa' variety of the *Spathiphyllum* species, the spathe coloration changing as the spathe matures to provide variegated blades that have a basic chlorophyllous field which contains chlorophyllous and nearly achlorophyllous streaks and blotches that are generally lighter in color than those found in the basic chlorophyllous field. 2. Immature spathe (shortly after initial expansion): (a) Midvein and blade tip areas — Commonly vivid yellowish green (17-9, 17-10, 18-8, 18-9, 18-10, 18-11, 19-7, 19-8, 19-9, 19-10, 19-11, 20-7, 20-8, 20-9, 20-10), deep yellowish green (17-11, 18-11, 19-12, 19-13, 20-11, 20-12, 20-13), vivid yellow green (21-9, 21-12, 22-10, 23-10), strong yellow green (21-11, 22-10, 22-11, and/or deep yellow green (21-12, 21-13). (b) Basic achlorophyllous field — Commonly very pale green (18-1, 19-1, 20-1), very light yellowish green (18-2, 19-2, 20-2), pale yellow green (21-1, 22-1, 23-1, 24-1), and/or light yellow green (21-2, 22-2, 23-2, 24-2). (c) Chlorophyllous streaks and blotches — Commonly vivid yellowish green (18-6, 18-7, 18-8, 19-6, 19-7, 19-8, 19-9, 19-10, 19-11, 20-7, 20-8, 20-9, 20-10), brilliant yellowish green (19-5), deep yellowish green (19-12, 19-3, 20-11, 20-12, 20-13), brilliant yellow green (20-5, 21-4, 21-5, 22-3, 22-4), vivid yellow green (20-6, 21-6, 21-7, 21-8, 21-9, 21-10, 22-5, 22-6, 22-7, 22-8, 22-9), and/or strong yellow green (21-11). 3. Mature spathe: (a) Basic chlorophyllous field (including blade tip areas) — Commonly vivid yellowish green (20-10), deep yellowish green (20-11, 20-12, 20-13), vivid yellow green (21-10, 22-10), strong yellow green (21-11, 22-10, 22-11, 22-12), deep yellow green (21-12, 21-13, 22-12), and/or moderate olive green (21-14, 22-13). (b) Achlorophyllous and chlorophyllous streaks or blotches — Commonly very pale green (19-1), very light yellowish green (19-2, 20-2), brilliant yellowish green (19-3, 19-4, 19-5, 20-3), vivid yellowish green (19-5, 19-6, 20-7, 20-8), pale yellow green (20-1, 21-1, 22-1, 23-1), brilliant yellow green (20-4, 20-5, 21-3, 21-4, 21-5, 22-3, 22-4, 23-3, 23-4), vivid yellow green (20-6, 21-6, 21-7, 21-8, 22-5, 22-6, 22-7, 23-5, 23-6), and/or light yellow green (21-2, 22-2, 23-2).

Stipe:

A. *General.*—Cylindrical, succulent, rigid and emerging from the midvein of the spathe at an acute angle to merge thereabove with the spadix.

B. *Texture.*—Smooth and glabrous.

C. *Shape.*—Terete.

D. *Size.*—1. Length: Usually 2–12 mm. 2. Diameter: Usually 2–5 mm.

E. *Color.*—Commonly strong yellow green (22-11, 22-12), and/or deep yellow green (22-12, 21-12).

Spadix:

A. *General.*—Ascendingly attached to the stipe and provided with a plurality of individual flowers that mostly project radially of the spadix axis.

B. *Shape.*—Generally cylindrical.

C. *Size.*—1. Diameter: Usually 10–16 mm. 2. Length: Usually 3–7 cm.

D. *Color.*—Commonly pale yellow green (24-1, 25-1) and/or pale greenish yellow (25-2) upon initial exposure and changing to pale yellowish green (26-1), pale greenish yellow (26-2) and/or pale yellow (27-1, 27-2) at the time of pollen presentation. This is followed by a gradual darkening and increase in saturation to strong yellow green (22-10) and/or vivid yellow green (21-9, 21-10, 22-10, 23-10) before withering and drying up.

E. *Flowers.*—1. General: Complete and perfect with the individual flowers being born distally of the stipe and in a contiguous helical arrangement about the axis of the spadix, the gynoecium having a dominating conical style that surmounts the surrounding and appressed androecium and perianth of the individual flowers. 2. Perianth: (a) General — With an actinomorphic calyx and corolla respectively composed of outer and inner tepals. (b) Calyx — (1) General: Composed of three clawed tepals. (2) Texture: Fleshy and glabrous. (3) Shape: Usually reniform above the claw and concave on adaxial side. (4) Size: Length usually about 1.5 mm. above the claw and about 3 mm. wide at the widest point above the claw, the claw being usually about 0.5 mm. long and varying in width above the insertion from about 1–1.5 mm. (5) Color: Commonly pale yellow green (26-1), pale greenish yellow (26-2), and/or pale yellow (27-1) at time of first exposure of spadix. (c) Corolla — (1) General: Composed of three tepals. (2) Texture: Fleshy and glabrous. (3) Shape: Broadly elliptical to orbicular with a concave adaxial surface. (4) Size: a. Length — Commonly 1–2 mm. b. Width — Commonly 1–2 mm. (5) Color: Commonly pale yellow green (22-1, 23-1, 24-1, 25-1), pale greenish yellow (25-2, 26-2), and/or pale yellow (27-1) at time of first exposure of spadix. 3. Androecium: (a) General — Usually six stamens with a broad filament and bilocular anthers that are retained within the concavity of a tepal until presentation and subsequent dehiscence, the stamens usually maturing sequentially in pairs that are respectively located at opposite sides of the geniculum and remain exserted following dehiscence. (b) Filaments — (1) Texture: Fleshy and glabrous during presentation. (2) Shape and Size: a. General — Elongated and flattened and lengthening during presentation. b. Length — Usually about 0.5–1.5 mm. in length prior to presentation and usually about 1.5–3 mm. after presentation and elongation. c. Width — Usually about 0.7–1.5 mm. before and after presentation. (3) Color: Commonly pale yellow green (26-1) and/or pale yellow (27-1) at time of first exposure of spadix. (c) Anthers — (1) General: Bilocular and born on a slender connective. (2) Texture: Fleshy and glabrous. (3) Shape: Oblong-ovoid pollen sacs. (4) Size: Pollen sacs are usually about 1–1.6 mm. long and about 0.3–0.4 mm. wide prior to dehiscence. (5) Color: Commonly pale yellow green (25-1) during pollen presentation and with pollen being commonly pale yellow green (25-1, 24-1). 4. Gynoecium: (a) General — Compound, ovoid to obclavoid, and glabrous pistils usually composed of three carpels subtended by the androecium and perianth. (b) Stigma — A triradiate groove at the summit of the pistil and barely visible to the unaided eye. (c) Style — (1) General: A conical extension from the ovary that protrudes beyond the surrounding proximate perianth parts of the spadix. (2) Texture: Fleshy and glabrous. (3) Shape: Conical. (4) Size: Usually 1–3 mm. for the exposed length after first exposure of the spadix. (5) Color: Commonly pale yellow green (25-1) and/or pale yellowish green (25-2) upon first exposure of the spadix and tending toward pale yellow (27-2) at the time of pollen presentation. (d) Ovary — (1) General — Superior, sulcate by virtue of concavities for anthers, and usually three carpellate with axile-basal placentation, and usually 2–4 oblong-ovoid ovules per carpel. (2) Texture — Fleshy and glabrous. (3) Shape — Generally pyriform and merging into the base of the style. (4) Size — Usually 2–3 mm. long from the insertion to the plane of the style exposure and 3–4 mm. diameter (maximum). (5) Color — Commonly light yellow green (24-2) and/or brilliant yellow green (24-3) prior to pollen presentation and usually being pale yellow green (21-1) during ovary maturation.

The following is a general description of a specimen of the new plant variety which was grown in a nursery at Fort Lawn, S.C. from a propagated stem cutting and wherein the description was taken in the month of November.

Age of specimen: 6 months from initial propagation.
Height of plant (mature leaves): 26 cm.
Diameter of plant (leaf spread): 42 cm.
Number of basal tillers: 5.
Number of expanded leaves on main axis: 11.
Number of leaves in vernation on main axis: 1.
Stems:

A. *Main axis.*—1. General: Surrounded by leaf bases. 2. Height: Rises approximately 3 cm. above the uppermost adventitious root. 3. Diameter: About 3 cm. (including leaf bases) at the root line.

B. *Tillers.*—1. General: Surrounded by leaf bases. 2. Diameter: 4 tillers with diameters (including leaf bases) of about 0.5 cm. and 1 tiller with a diameter (including leaf bases) of about 1 cm.

Leaves:

A. *Petioles.*—1. Diameter (intermediate sheath and geniculum): Ranges from about 2–3 mm. for immature leaves to 3–4 mm. for mature leaves. 2. Length: 11–18 cm. in overall length for the leaf petioles on the main axis, 7–13 cm. for the lengths of the petiole sheaths on the main axis and 2–14 cm. in length for the petiole genicula on the main axis. 3. Color (main axis petioles): (a) Area proximate to geniculum — Dark yellowish green (19-14), moderate olive green (21-14). (b) Geniculum — Deep yellow green (21-12, 22-12), strong yellow green (21-11, 22-11).

B. *Midrib colors.*—1. Adaxial side: Moderate olive green (22-13), dark olive green (20-15). 2. Abaxial side: Deep yellow green (21-12), strong yellow green (21-11).

C. *Blades.*—1. Length: 16–23 cm. between proximal and distal ends. 2. Width (maximums): 6–8 cm. 3. Color: (a) Basic chlorophyllous field — Moderate olive green (22-13), dark olive green (20-15), dark yellow green (21-13), dark yellowish green (20-14), and/or deep yellow green (22-12). (b) Streaks and splotches — Brilliant yellow green (22-3, 22-4), vivid yellow green (21-6, 22-8), strong yellow green (22-10, 22-12), light yellow green (23-2), and/or vivid yellow green (20-8, 19-9).

Inflorescence:

A. *Peduncle.*—1. Size: (a) Length — 38 cm. (b) Diameter — About 5 mm. at emergence from sheath and about 4 mm. near spathe. 2. Color: Strong yellow green (21-11).

B. *Spathe.*—1. Size: (a) Length — 14 cm. (b) Width — 6.5 cm. (max.) when flattened. (c) Depression depth — 2.5 cm. 2. Color: (a) During immaturity — (1) Midvein and blade tip area: Strong yellow green (21-11), vivid yellow green (21-9). (2) Basic achlorophyllous field: Very pale green (20-1), pale yellow green (21-1). (3) Chlorophyllous streaks and blotches: Vivid yellow green (19-6, 19-7), brilliant yellowish green (19-5), brilliant yellow green (20-5). (b) Mature spathe — (1) Basic chlorophyllous field: Deep yellowish green (21-12, 22-12), strong yellow green (22-12). (2) Achlorophyllous and chlorophyllous streaks and blotches: Pale yellow green (20-1), brilliant yellow green (21-3), vivid yellow green (21-7).

C. *Stipe.*— 1. Size: (a) Diameter — About 4 mm. (b) Length — About 5 mm. 2. Color: Strong yellow green (21-11).

D. *Spadix.*—1. Size: (a) Diameter — About 15 mm. (b) Length — About 6 cm. 2. Color: Pale yellow green (25-1) at time of spathe expansion, pale yellowish green (27-1) at time of pollen presentation, and ultimately vivid yellow green (21-9) before withering.

E. *Flowers.*—1. Perianth: (a) Calyx — (1) Size: a- Length — About 1.5 mm. above the claw and with the claw length of about 0.5 mm. b- Width — About 3 mm. at widest point above the claw and with the claw width being 1–1.5 mm. (2) Color: Pale yellow green (26-1) at time of first exposure. (b) Corolla — (1) Size: a- Length — 1–2 mm. b- Width — 1–2 mm. (2) Color: Pale yellowish green (26-2) at time of first exposure. 2. Androecium: (a) Filaments — (1) Size: a- Length — About 0.5–1.5 mm. before lengthening to about 1.5–3 mm. after presentation. b- Width — About 0.7–1.5 mm. (2) Color: Pale yellow green (26-1). (b) Anthers — (1) Size (before dehiscence): a- Length — About 1–1.5 mm. b- Width — About 0.3–0.4 mm. (c) Color: Pale yellow green (25-1). 3. Gynoecium: (a) Style — (1) Size: About 1–3 mm. exposed after spathe expansion. (2) Color: Pale yellowish green (25-2) at time of first exposure of spadix. (b) Ovary — (1) Size: a- Length — About 2.5 mm. from insertion to plane of exposed part of style. b- Width (max.) — About 3.5 mm. (2) Color: Brilliant yellow green (24-3).

I claim:

1. The new and distinct variety of the Araceae family as described and illustrated and which combines the following principal distinguishing characteristics:

(1) a plant specimen which in size is generally smaller than those of the 'Mauna Loa' variety of the *Spathiphyllum* species, (2) foliage that includes leaf blades which are variegated and provided with a basic chlorophyllous field that contains streaks and blotches which in colors are generally lighter than those of the basic chlorophyllous field and which also vary in color, pattern and size within the leaf blades and from one leaf blade to the next, and (3) an inflorescence with a spathe that shortly after initial expansion is provided with variegated blades which have a basic achlorophyllous field that contains chlorophyllous streaks and blotches and merges distally in the spathe with a chlorophyllous tip area which extends proximally in the leaf blade further than that of the 'Mauna Loa' variety of the *Spathiphyllum* species, the spathe coloration changing as the spathe matures to provide variegated blades that have a basic chlorophyllous field which contains chlorophyllous and nearly achlorophyllous streaks and blotches that are generally lighter in color than those found in the basic chlorphyllous field.

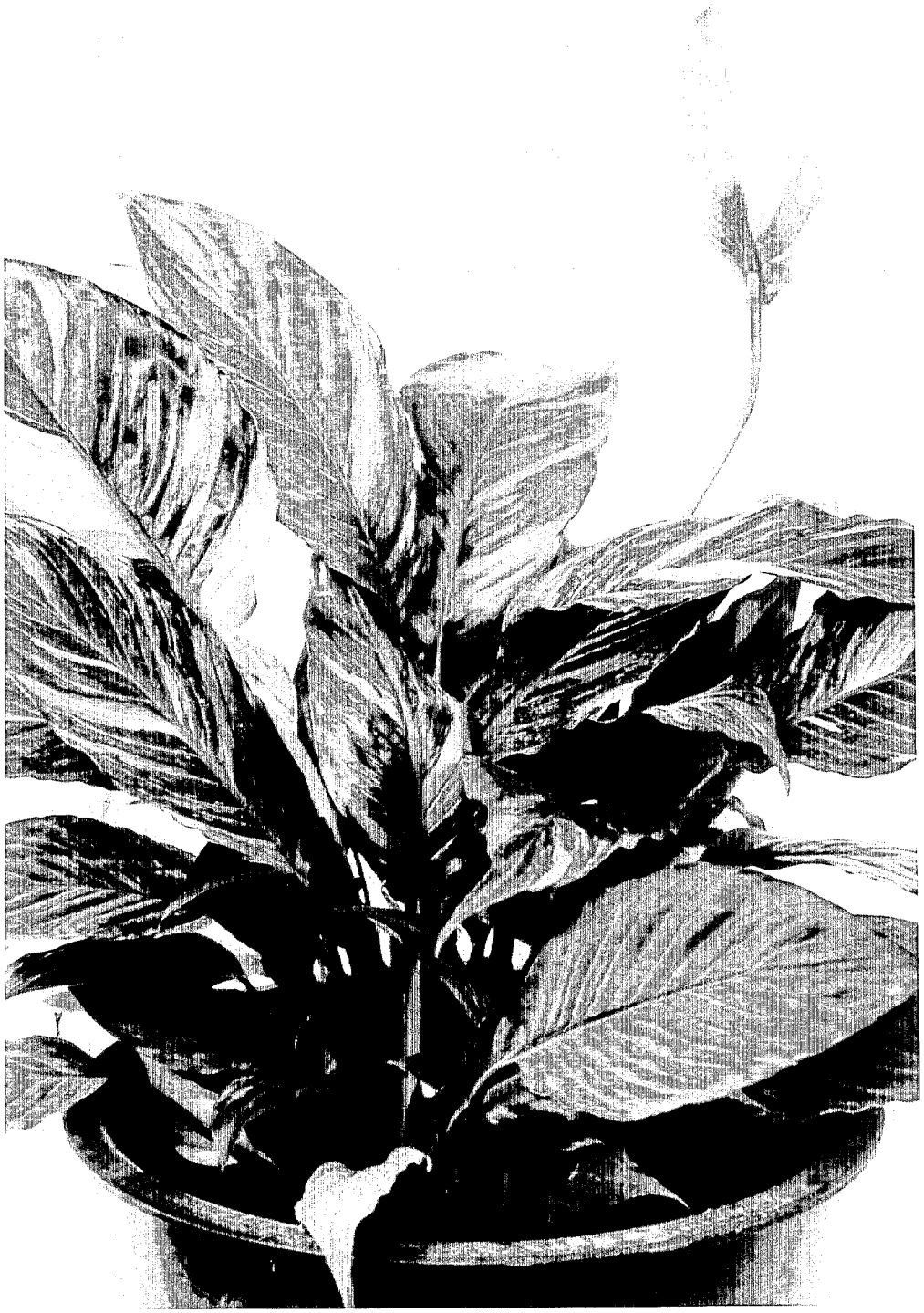

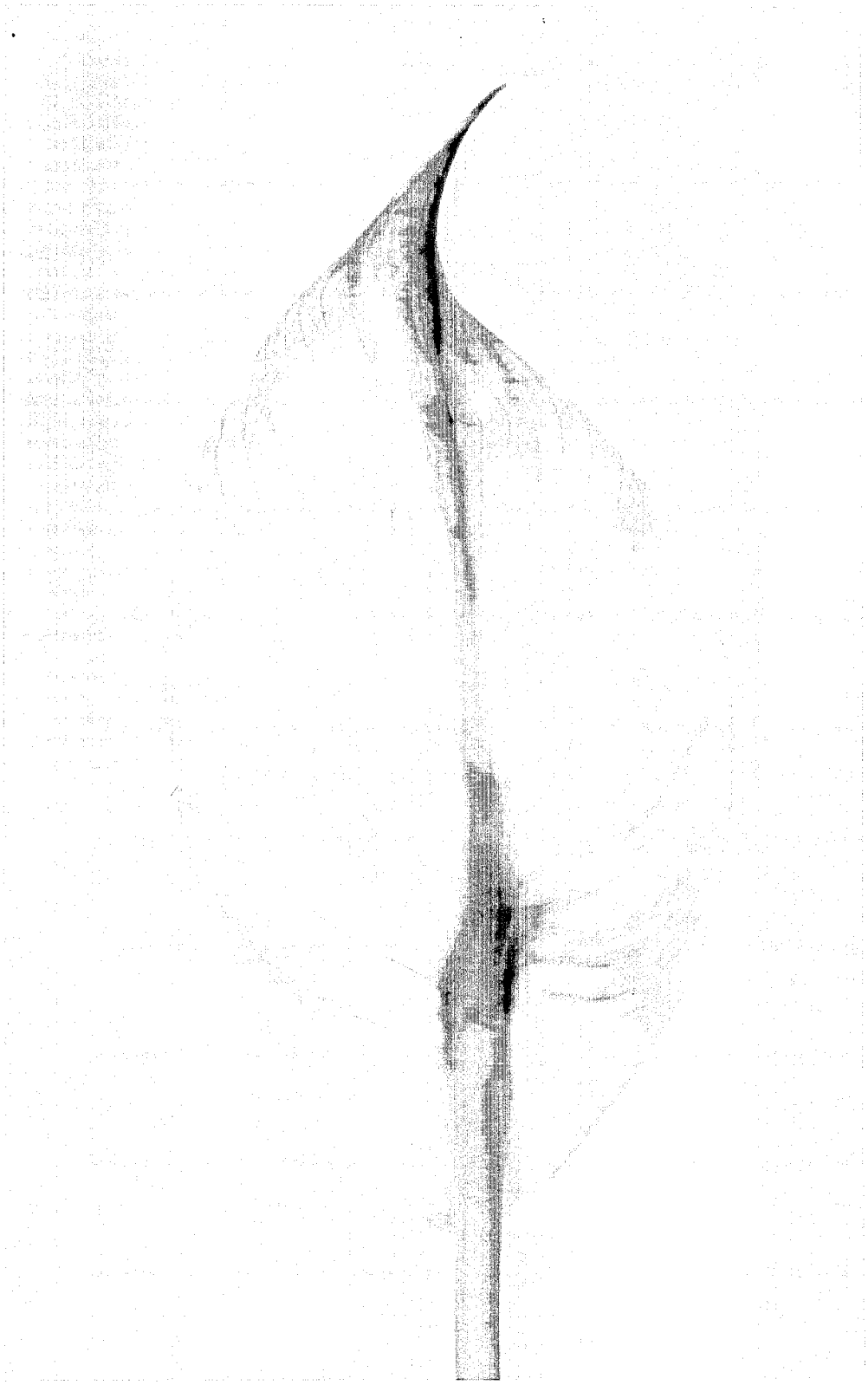

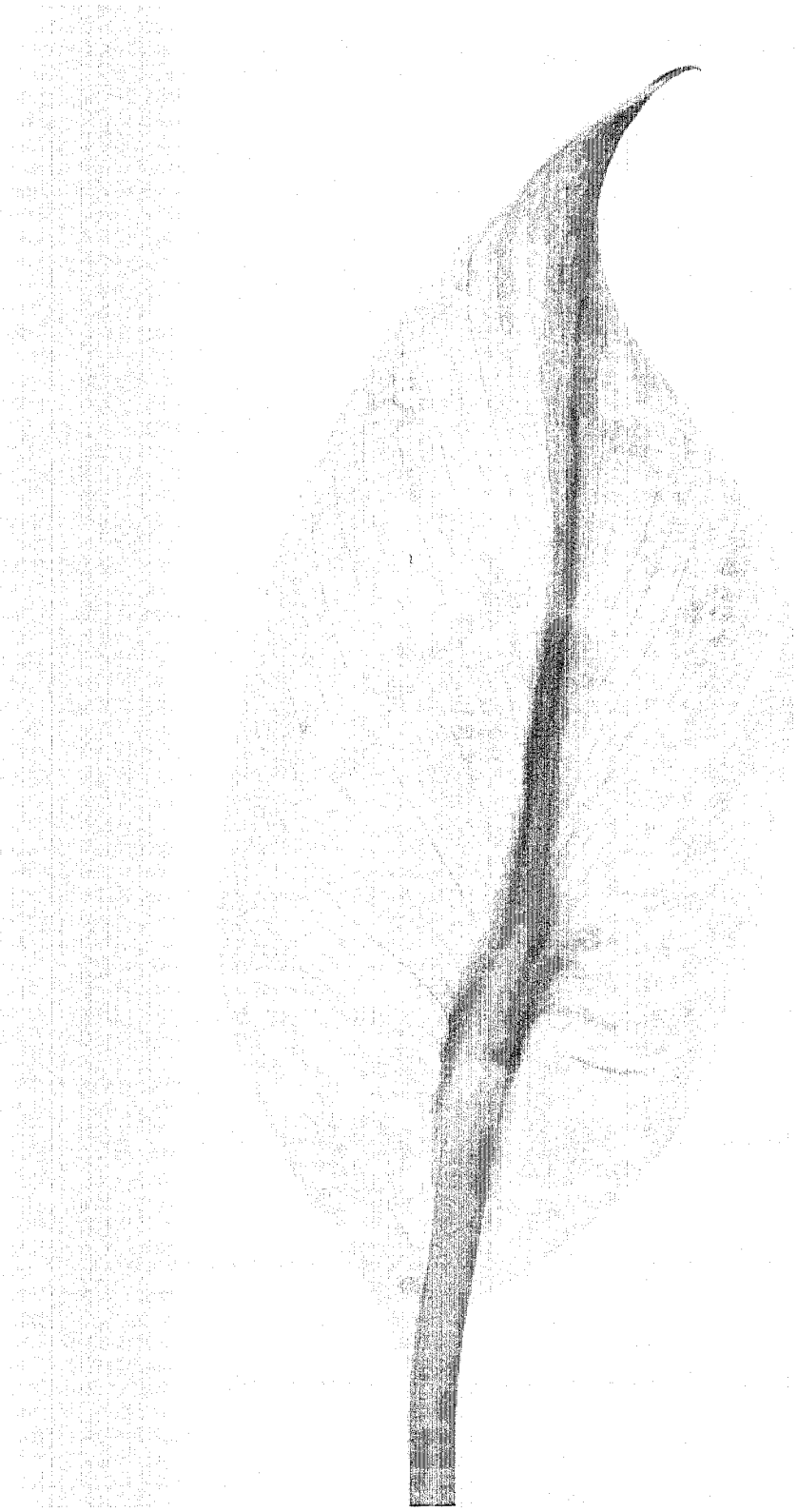

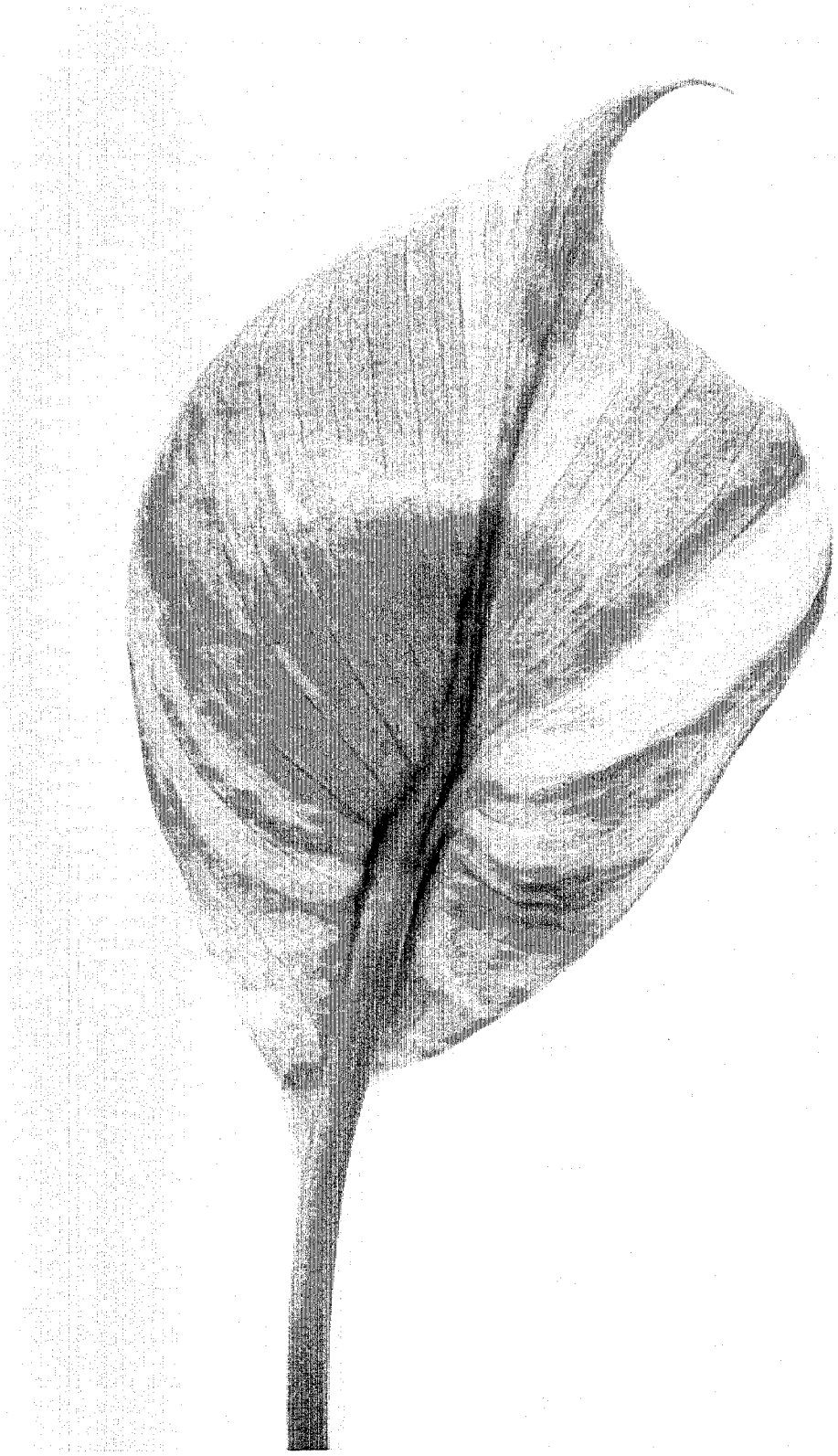

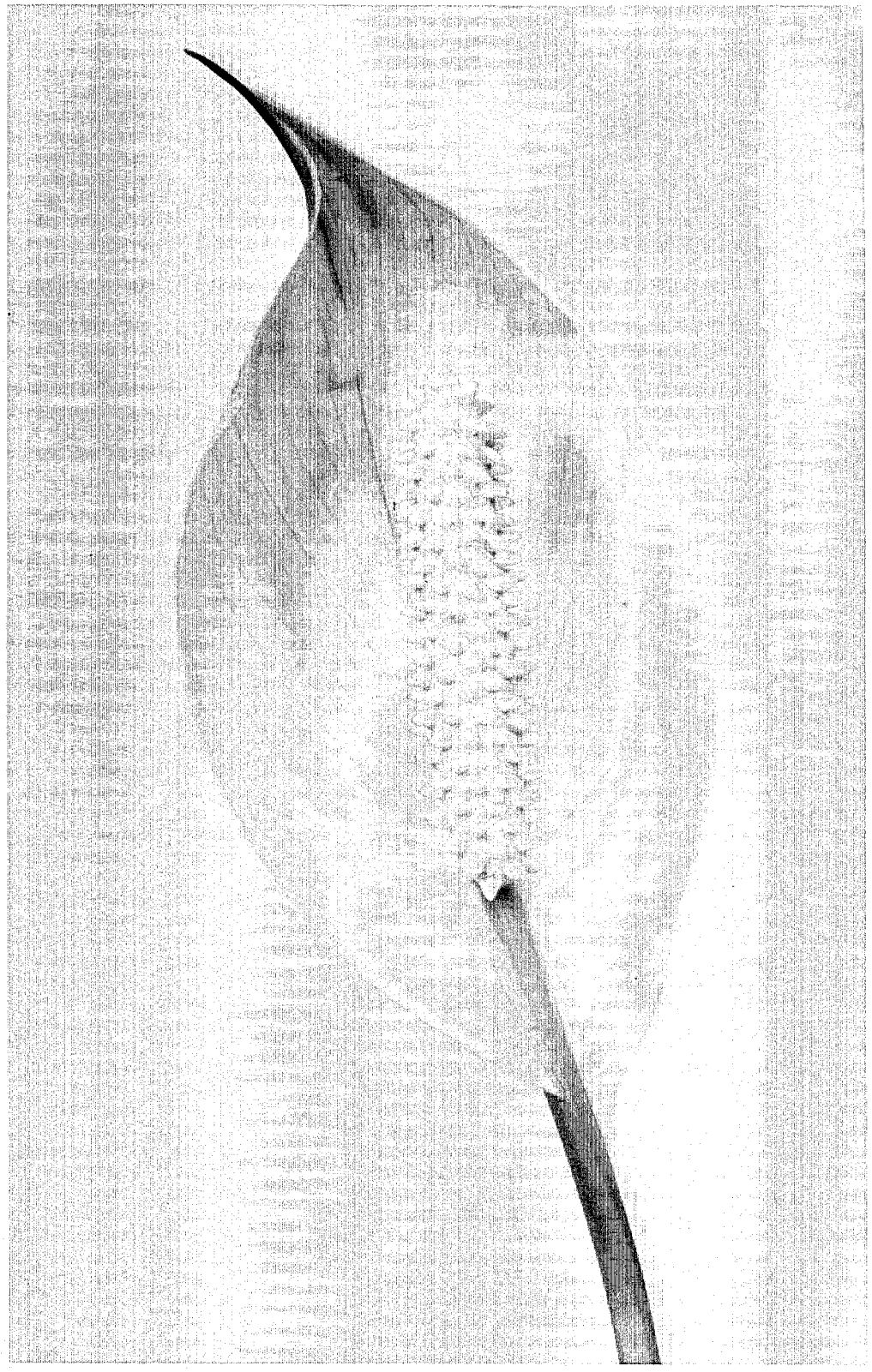

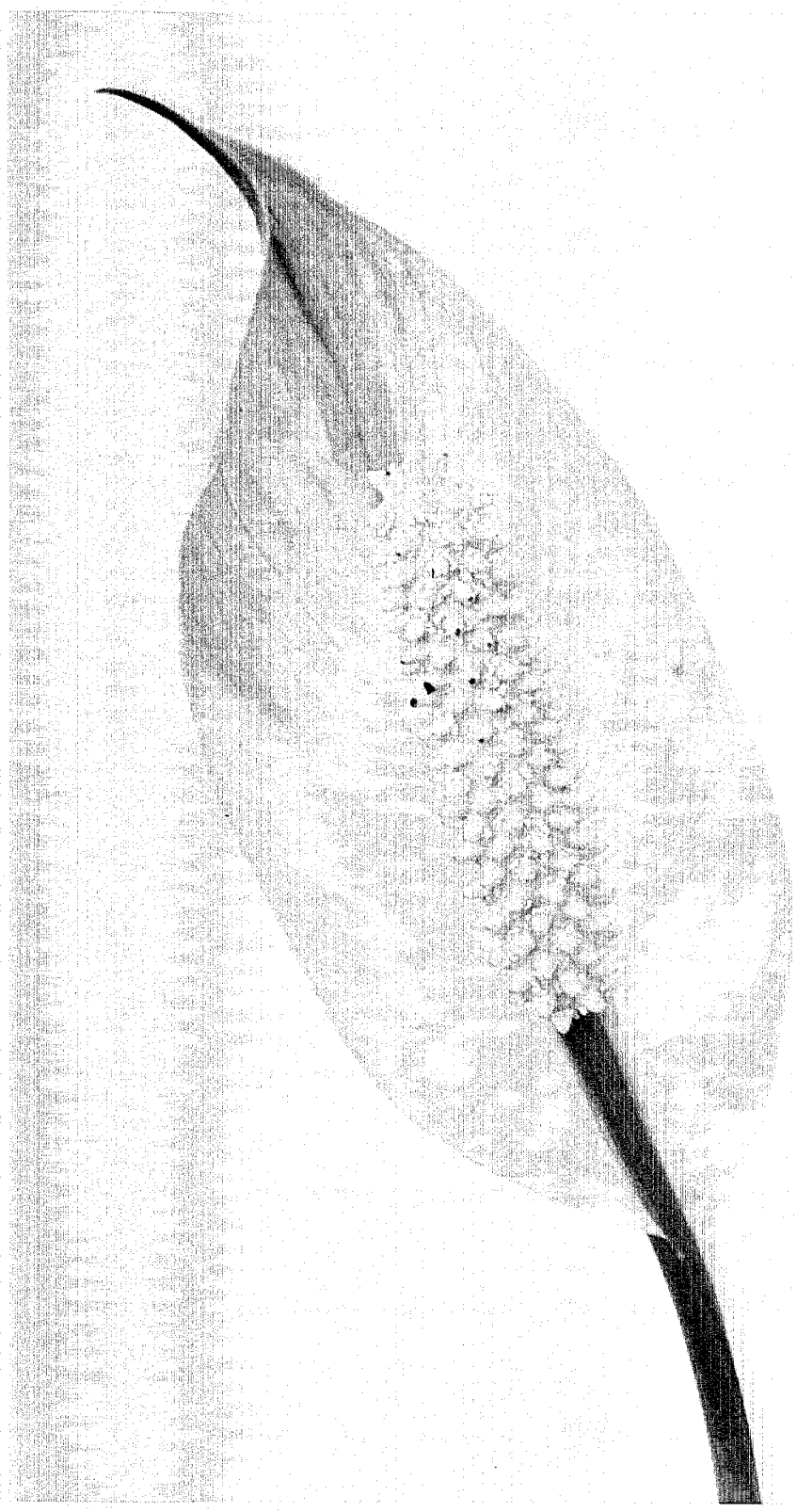

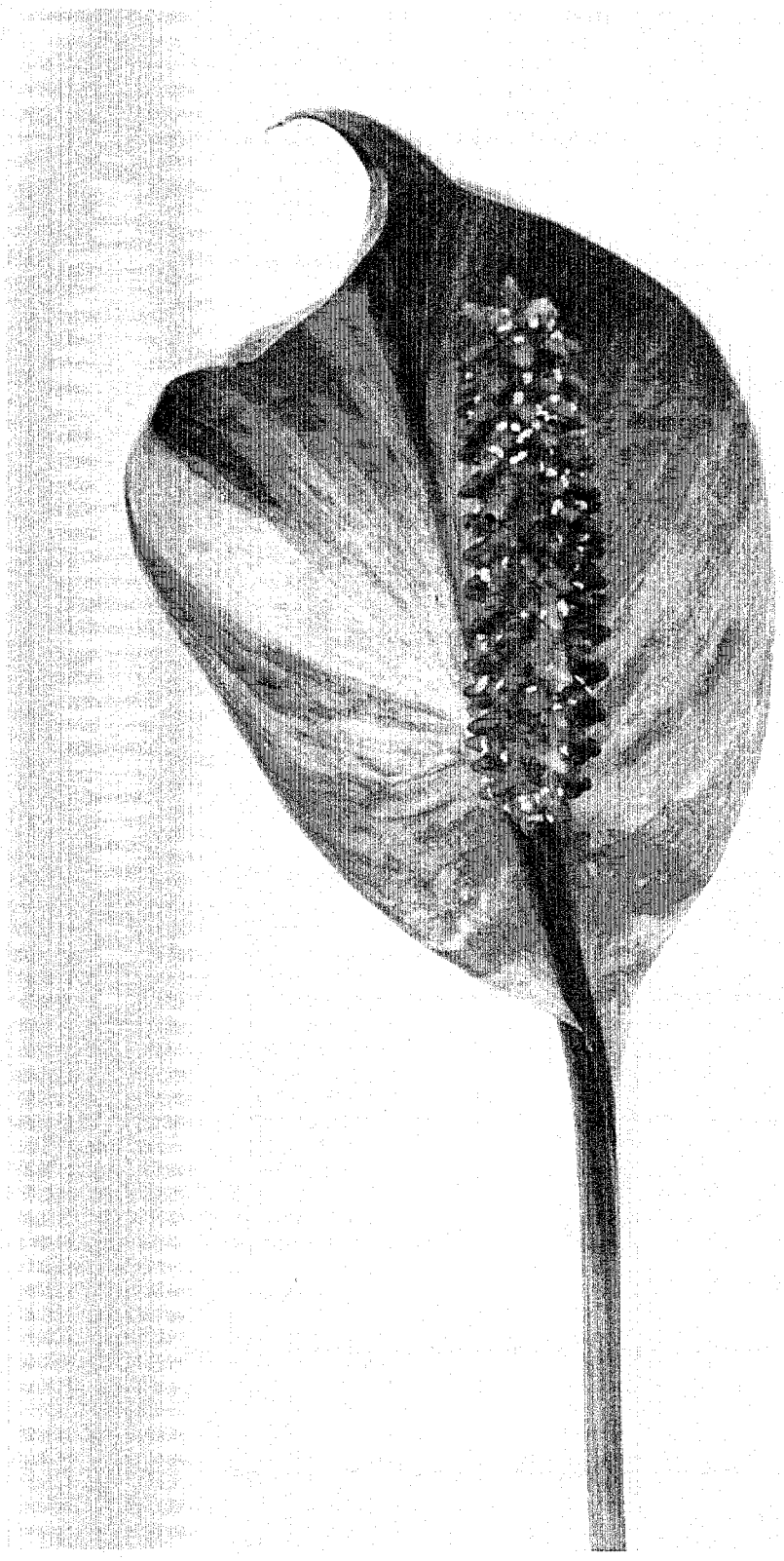

* * * * *